United States Patent
Chulick

[19]

[11] Patent Number: 5,932,093
[45] Date of Patent: Aug. 3, 1999

[54] CHLORINE DISPENSER

[76] Inventor: Joe Chulick, 6245 Oak Ridge Dr., Flowery Branch, Ga. 30542

[21] Appl. No.: 09/016,036

[22] Filed: Jan. 30, 1998

[51] Int. Cl.[6] .................................. B01F 1/00; C02F 1/50
[52] U.S. Cl. ..................... 210/169; 210/198.1; 210/86; 210/91; 210/94; 422/261; 422/263; 422/265; 422/266; 422/276; 137/268
[58] Field of Search ................................. 210/169, 198.1, 210/86, 91, 94; 422/261, 263, 265, 266, 276; 137/268

[56] References Cited

U.S. PATENT DOCUMENTS

| | | |
|---|---|---|
| 2,934,409 | 4/1960 | Biehl . |
| 3,710,817 | 1/1973 | Lorenzen . |
| 3,765,534 | 10/1973 | West et al. . |
| 4,199,001 | 4/1980 | Kratz . |
| 4,208,376 | 6/1980 | Sangster . |
| 4,420,394 | 12/1983 | Lewis . |
| 4,548,227 | 10/1985 | Regunathan et al. . |
| 4,606,893 | 8/1986 | Sangster . |
| 4,662,387 | 5/1987 | King, Sr. . |
| 4,691,732 | 9/1987 | Johnson et al. . |
| 4,825,528 | 5/1989 | Nicholson . |
| 4,867,196 | 9/1989 | Zetena et al. . |
| 5,053,206 | 10/1991 | Maglio et al. . |
| 5,089,127 | 2/1992 | Junker . |
| 5,251,656 | 10/1993 | Sexton, Sr. . |
| 5,384,102 | 1/1995 | Ferguson et al. . |
| 5,385,044 | 1/1995 | Thomas et al. . |
| 5,417,233 | 5/1995 | Thomas . |
| 5,441,711 | 8/1995 | Drewery . |
| 5,507,945 | 4/1996 | Hansen . |

*Primary Examiner*—Thomas M. Lithgow
*Attorney, Agent, or Firm*—Kenneth L. Tolar

[57] ABSTRACT

The present invention relates to a new and improved chlorine dispenser including a substantially cylindrical housing having a closed bottom and an open top in communication with an interior chamber. A pair of diametrically opposed apertures are disposed adjacent the bottom end for respectively receiving a water inlet and a water outlet pipe. A dial is rotatably mounted to the exterior surface of the housing immediately adjacent the bottom end. The dial is in communication with a valve means disposed within the water effluent line allowing the water flow through the interior chamber to be selectively adjusted. An elongated tubular shaft is received within the cylindrical housing and vertically depends from its bottom surface. On the exterior of the shaft is a switch means in communication with an output means which may be connected to an external or auxiliary alarm. A chlorine container is vertically slidable along the tubular shaft and gradually ascends to engage the switch means upon the amount of chlorine therein dissipating below a predetermined level. Accordingly, a user is audibly or visually alerted whenever the chlorine remaining in the container has diminished to a predetermined amount thereby notifying the user that the dispenser must be reloaded.

9 Claims, 2 Drawing Sheets

CHLORINE DISPENSER

BACKGROUND OF THE INVENTION

The present invention relates to a chlorine dispensing unit for swimming pools, and more specifically, a dispenser having an output means for signalling an external alarm which is automatically activated upon the amount of chlorine in the dispenser diminishing below a predetermined level.

DESCRIPTION OF THE PRIOR ART

Chlorine in various forms is typically added to a swimming pool to control the growth of algae and other microbiological organisms. Because the handling and storage of gaseous chlorine is dangerous and difficult, granular chlorine material such as calcium hypochlorite is typically used in swimming pool applications. Typically, the dry chlorine material is placed in a chlorinator storage chamber and water is passed therethrough to form a chlorine solution. The resulting solution is then routed to the swimming pool. Because water is continuously flowing through the chlorine dispensing device, a user must frequently refill the dispenser with chlorine granules. However, because the chlorine dissolution rate may vary depending upon water flow, temperature, pressure and many other factors, it is difficult to predict when the chlorinator needs reloading. A user must then frequently inspect the storage chamber to determine the amount of chlorine tablets remaining. If the user fails to regularly inspect the unit, chlorine feed to the swimming pool may be interrupted, perhaps for an extended period of time. In such event, algae and other microbiological organisms can bloom out of control. Therefore, there is currently a need for a chlorine dispensing device which readily alerts a user when the amount of available dry granular material therein has dissipated to a predetermined level.

Although chlorine dispensing devices exist in the prior art, none of these devices relate to a chlorinator capable of communicating with an external alarm means to notify a user that the chlorinator needs to be reloaded. For example, U.S. Pat. No. 4,420,394 issued to Lewis discloses a pool chlorinator comprising a sealed chamber having a granular chlorine container. The container has a vertically moving sleeve forming a side wall and a fixed platform forming the bottom. Water from the pressure side of the pool pump flows across the top of the platform to dissolve the chlorine granules and to form a bridge of chlorine material in the sleeve above the water. The sleeve is lowered incrementally each time the pump is activated to move the caked material into dissolving contact with the flowing water.

U.S. Pat. No. 5,441,771 issued to Drewery discloses a chlorinator having water diverters designed to create consistent and even erosion of the chlorine tablets.

U.S. Pat. No. 5,507,945 issued to Hanson relates to a chemical dispenser for inserting into a water flow line.

U.S. Pat. No. 4,867,196 issued to Zitina discloses a pool chemical dispenser having three separate chambers to achieve uniform and controlled release of calcium hypochlorite.

U.S. Pat. No. 5,251,656 issued to Sexton, Sr. relates to a chemical feeder for swimming pools having two independent feeder compartments, a first for retaining a solid material and a second for retaining a liquid. Water flow through the device may be selectively controlled using an adjustable control means.

U.S. Pat. No. 5,384,102 issued to Ferguson discloses a chemical feeder for delivering controlled amounts of chlorine tablets or another similar chemical. As indicated above, none of the prior art chlorinating devices relate to a chlorine feeder capable of alerting a user that the amount of granular chlorine remaining therein is below a predetermined threshold level. The present invention provides such a device having a universal output connector allowing the device to be connected with any one of a number of external audible or visual alarms. Additionally, the device is enclosed with a transparent cap allowing a user to inspect the contents without opening or otherwise manipulating the device.

SUMMARY OF THE INVENTION

The present invention relates to a chlorine dispensing apparatus that overcomes the disadvantages of conventional swimming pool chlorine feeders enumerated above. The device comprises a cylindrical hollow housing having a closed bottom end and an open top end. Adjacent the open top end is an externally threaded portion for threadedly engaging a transparent cap. Adjacent the bottom end of the container are a pair of diametrically opposed apertures for receiving a water inlet and an outlet pipe. Mounted to the exterior of the housing, preferably proximal the closed end, is a dial selectively rotatable between a plurality of positions. The dial is in communication with a valve means disposed within the water effluent line for controlling the amount of water flow therethrough and thus the chlorine dissolution and feed rate to the swimming pool. Received within the cylindrical housing is a vertically disposed elongated tubular shaft. Extending outwardly from the shaft is a switch means vertically slidable between a first and a second position in electrical communication with an output means disposed on the exterior surface of the housing. The output means may be selectively connected to an external alarm to notify a user that the weight of the granular chlorine remaining in a container is below a predetermined value.

A cylindrical chlorine container is received within the housing having a continuous, circular perforated sidewall, an open top and a perforated bottom surface allowing water to permeate the container. Vertically extending the bottom surface, concentric with the circular sidewall, is an elongated tubular sleeve dimensioned to slidably receive the shaft. Accordingly, the chlorine container may freely slide vertically along the shaft dependant upon the water flow and the amount of chlorine in the container. As the chlorine in the container dissolves, the container will gradually rise until its sleeve displaces the switch means thereby sending a signal to the output means. It is therefore an object of the present invention to provide a chlorine dispensing unit that automatically alerts a user when the dispensing unit needs reloading.

It is yet another object of the present invention to provide a chlorine dispensing unit capable of dispensing a desired amount of chlorine.

It is yet another object of the present invention to provide a chlorine dispensing unit which may be selectively connected to an external alarm means.

It is yet another object of the present invention to provide a chlorine dispensing unit that is enclosable with a transparent cap allowing a user to visually determine the amount of chlorine contained therein. Other objects, features and advantages of the present invention will become readily apparent from the following detailed description of the preferred embodiment when considered with attached drawings and the appended claims.

DESCRIPTION OF THE PREFERRED EMBODIMENT

Figure 1:
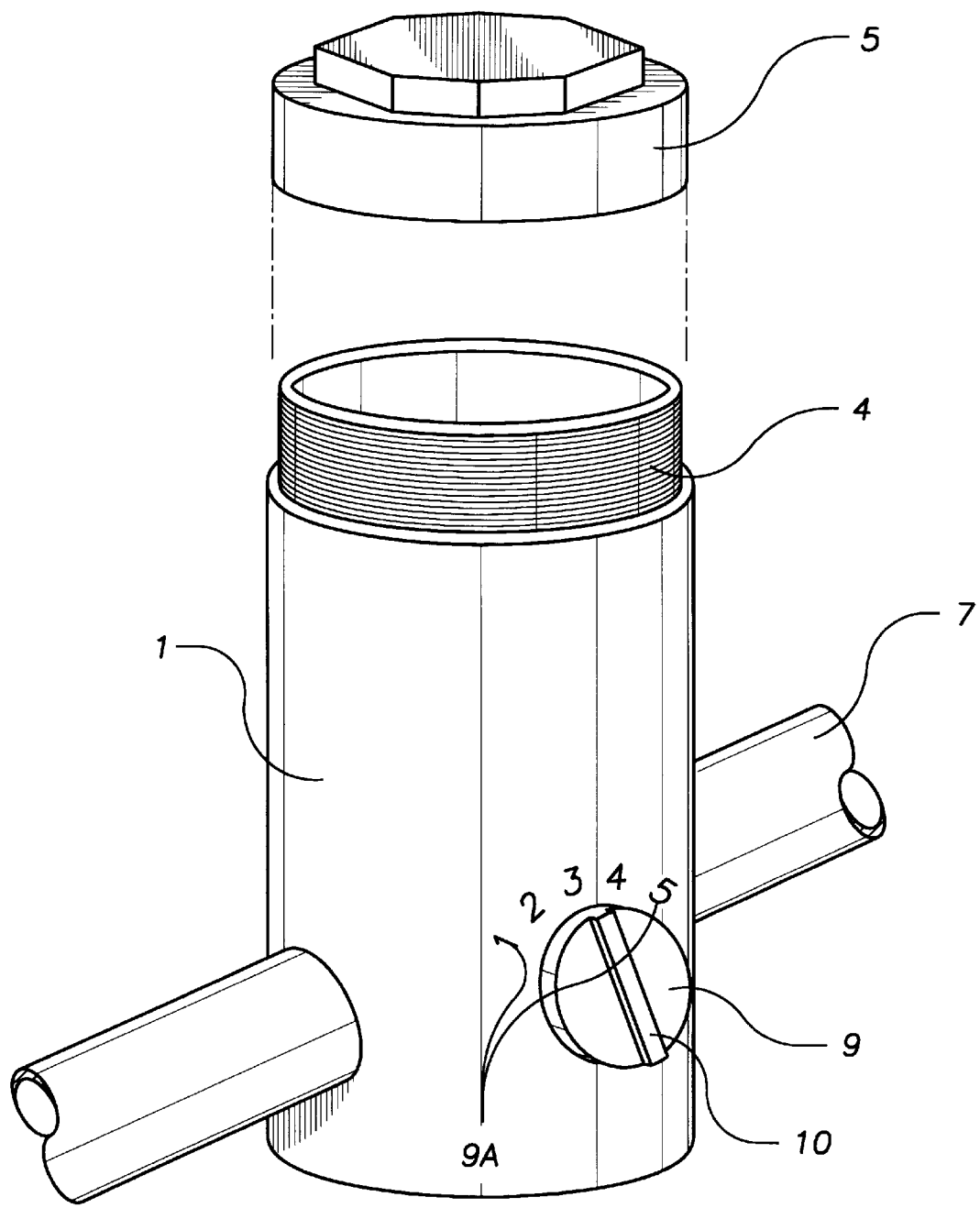
FIG. 1 depicts the inventive device.
Figure 2:
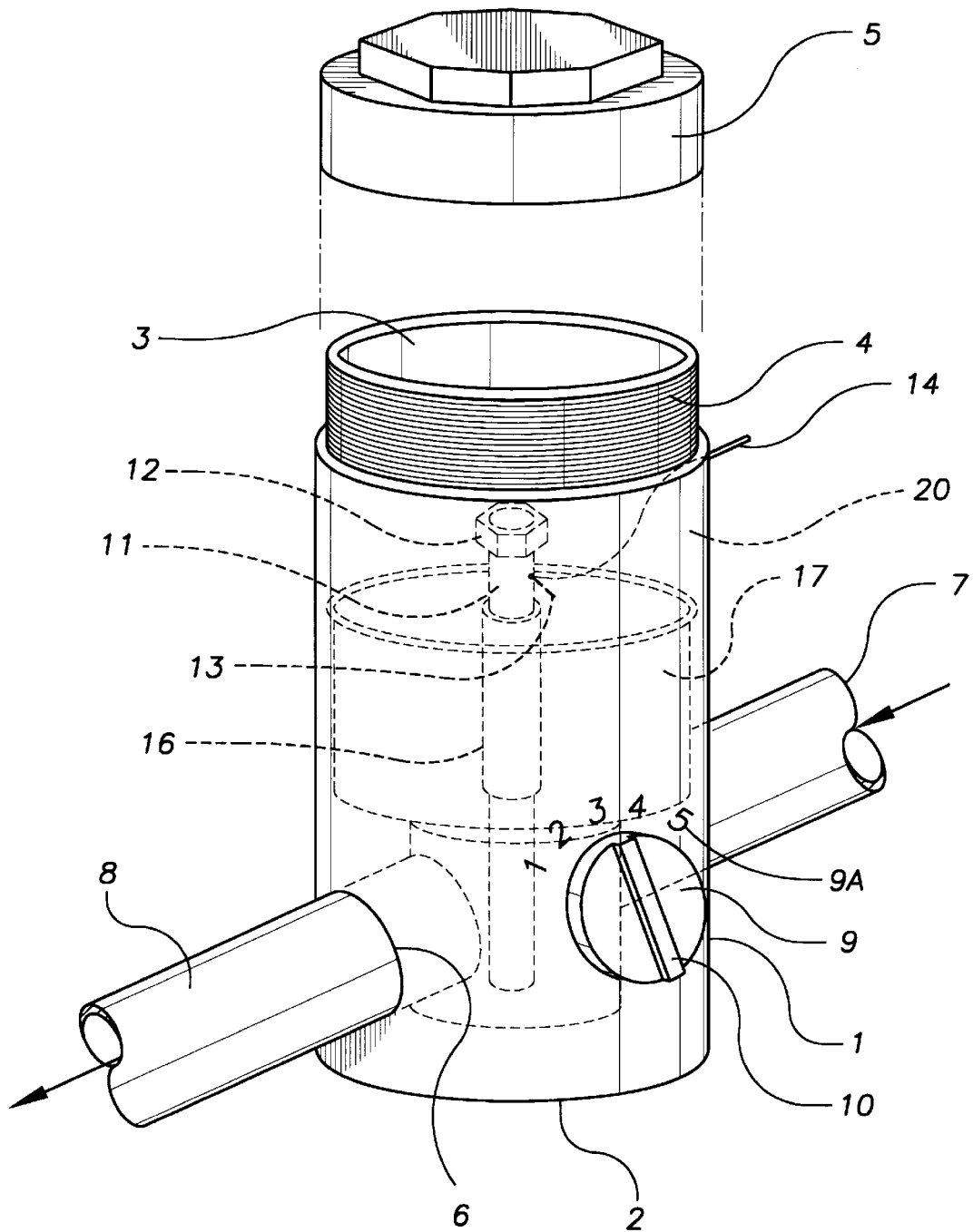
FIG. 2 depicts the inventive device with the internal components depicted in phantom.

Referring now to FIGS. 1 and 2, the present invention relates to a new and improved chlorine dispenser capable of communicating with an external alarm means to visually or audibly notify a user that the amount of chlorine contained therein is below a predetermined amount. The device comprises a cylindrical hollow housing 1 having a closed bottom end 2 and an open top end 3 in communication with an interior chamber 20. Around the exterior of the housing immediately adjacent the open end is an externally threaded portion 4 for threadedly engaging a circular cap 5. The cap 5 provides a water tight seal and is preferably constructed with a transparent material allowing a user to visually determine the amount of chlorine contained within the interior chamber.

Proximal the closed end are a pair of diametrically opposed apertures 6 in communication with the interior chamber. A water inlet conduit 7 preferably from a swimming pool recirculation pump is attached to a first aperture. A second effluent conduit 8 routed to the swimming pool is attached to the second aperture for delivering a chlorine solution thereto. The conduits typically relate to PVC piping or a similar liquid transport means.

A circular dial 9 having a direction indication means 10 thereon is rotatably attached to the housing exterior and is in communication with a mechanical valve means (not pictured) disposed within the water effluent line. The valve means received within the water effluent line may be any conventional valve of the type generally known in the prior art for throttling or adjusting water flow.

The dial 9 is selectively rotatable between a plurality of positions each corresponding to a select valve position for adjusting the water flow through the interior chamber. Preferably, a plurality of numerical indicia 9A are peripherally disposed about the dial to visually indicate to a user the selected valve position. Accordingly, the amount of water flowing through the housing and thus the rate at which chlorine dissolves and the amount delivered to a swimming pool may be selectively controlled.

Coaxially received within the housing 1 and attached to the interior surface of the bottom end 2 is an elongated shaft 11 having a stop means 12 at a distal end. Preferably, the stop means is a nut threadedly engaging the tubular shaft allowing the position of the stop means to be selectively adjusted. The stop means may then be removed in order to remove the chlorine container. Immediately below the stop means 12 is a switch means 13 vertically pivotable between a first and a second position. The switch means 13 is in electrical communication with an output means 14 such as an electrical connector for engaging a similar connector on an external or auxiliary alarm means. The output means 14 is preferably disposed on the exterior surface of the cylindrical housing 60 providing convenient access thereto. The electrical connector is of the type generally known in the prior art and typically comprises a water proof plug type connector for matably connecting a similar connectior on an audible or visual alarm. The output means provides greater versatility allowing the device to be interchangeably used with a select one of a variety of external alarms. The device also has a signal source such as a battery means (not pictured) for transmitting a signal to the external alarm upon actuation of the switch.

Also received within the cylindrical housing is a chlorine container 17 having a perforated circular bottom surface, a perforated circular side wall perpendicularly depending therefrom and an open top. Vertically extending from the bottom surface is an elongated concentric tubular sleeve 16 for receiving the shaft 11. Accordingly, the chlorine container may slide along the shaft depending upon the amount of chlorine contained therein and the water flow rate through the housing. The stop means, however, will prevent the container from being completely dislodged from the shaft.

To use the above described device, a user removes the transparent cap and places a predetermined amount of chlorine tablets into the chlorine container. The cap is replaced and the water flow through the cylindrical housing is established. The circular dial is set to a select position according to a desired chlorine feed rate. The chlorine tablets within the container will be gradually dissolved and the resulting solution is delivered to the swimming pool via the effluent water line. As the chlorine dissolves and the amount remaining in the container dissipates, the chlorine container will begin ascending along the elongated shaft until it eventually contacts and upwardly displaces the switch means. Electrical communication between the switch means and the output means will then be established and an external alarm attached thereto will be activated. Accordingly, a user may attach a desired alarm means to the output connector which will either audibly or visually alert the user upon the chlorine level dissipating below a predetermined level.

The device is not to be limited to the exact details enumerated above. The size, shape and materials of construction of the various components may vary. However, it is preferred that the various components of the inventive device be manufactured with plastic or a similar lightweight, corrosion resistant material.

Although there has been shown and described the preferred embodiment of the present invention, it will be readily apparent to those skilled in the art that modifications may be made thereto which do not exceed the scope of the appended claims. Therefore, the scope of the invention is only to be limited by the following claims.

What is claimed is:

1. A chlorine dispenser for delivering a chlorine solution to a swimming pool comprising:

a hollow cylindrical housing having a closed bottom end, an open top end in communication with an interior chamber and a pair of diametrically opposed apertures on the exterior of said housing, each aperture for respectively receiving a water inlet conduit and a water outlet conduit;

an elongated tubular shaft, having two opposing ends, vertically received within said interior chamber with a first end attached to the interior surface of the housing bottom end;

a switch means on the exterior surface of the tubular shaft pivotable between a first and a second position;

an output means in selective electrical communication with the switch means, said output means disposed on the exterior surface of the cylindrical housing for selectively communicating with an external alarm upon the switch means pivoting to a first position;

a granular chlorine container for receiving a plurality of dry chlorine containing granules vertically slidable along said tubular shaft for engaging said switch means upon the weight of the chlorine material contained therein dissipating to a predetermined level.

2. A chlorine dispenser according to claim 1 further comprising means for selectively delivering a predetermined amount of water to said interior chamber.

3. A chlorine dispenser according to claim 2 wherein said means for delivering a predetermined amount of water to said interior chamber comprises a dial rotatably mounted on the exterior surface of the cylindrical housing in communication with a valve means disposed within the water outlet conduit for selectively throttling the amount of water flow through the interior chamber.

4. A chlorine dispenser according to claim 1 further comprising a cap threadedly engaging the open end of the cylindrical housing for selectively enclosing the housing interior chamber.

5. A chlorine dispenser according to claim 1 wherein said chlorine container comprises a substantially circular perforated bottom surface with a continuous perforated circular sidewall vertically depending therefrom and an elongated tubular sleeve for slidably receiving the tubular shaft vertically depending from the bottom surface and concentrically disposed within said circular wall.

6. A chlorine dispenser according to claim 1 wherein the tubular shaft has a stop means at a distal end for retaining the chlorine container thereon.

7. A chlorine dispenser according to claim 4 wherein said cap is transparent allowing a user to visually inspect the interior chamber.

8. A chlorine dispenser according to claim 1 wherein said output means comprises a plug type connector for selectively engaging a similar plug type connector on an external alarm.

9. A chlorine dispenser according to claim 6 wherein said stop means is a nut threadedly engaging said tubular shaft allowing the position of the stop means relative to the shaft to be selectively adjusted.

\* \* \* \* \*